United States Patent [19]

Stark et al.

[11] Patent Number: 5,491,250

[45] Date of Patent: Feb. 13, 1996

[54] PROCESS FOR PURIFYING VINYLICALLY UNSATURATED COMPOUNDS PREPARED USING A PALLADIUM-COMPLEX CATALYST

[75] Inventors: Edmund J. Stark, Midland; John A. Schultz, Auburn; Ernest L. Ecker; Robert A. DeVries, both of Midland, all of Mich.

[73] Assignee: The Dow Chemical Company, Midland, Mich.

[21] Appl. No.: 409,115

[22] Filed: Mar. 23, 1995

[51] Int. Cl.⁶ .................................................. C07F 7/08
[52] U.S. Cl. .................. 556/466; 585/435; 585/638; 585/641; 585/642; 560/205; 556/450; 556/453; 210/656; 203/99
[58] Field of Search .................................. 556/466, 450, 556/453; 585/435, 638, 641, 642; 210/656; 203/99

[56] References Cited

U.S. PATENT DOCUMENTS

| 3,922,299 | 11/1975 | Heck | 260/476 |
|---|---|---|---|
| 4,658,071 | 4/1987 | Seufert et al. | 556/466 X |
| 4,822,930 | 4/1989 | Liu | 570/206 |
| 5,138,081 | 8/1992 | DeVries et al. | 556/466 |
| 5,243,068 | 9/1993 | DeVries et al. | 560/205 |
| 5,264,646 | 11/1993 | DeVries et al. | 585/641 |
| 5,424,470 | 6/1995 | Bank et al. | 556/479 |

OTHER PUBLICATIONS

Heck, Richard F., *Palladium–Catalyzed Vinylation of Organic Halides*, Organic Reactions, vol. 27, pp. 345–390 (1982).

*Primary Examiner*—Paul F. Shaver
*Attorney, Agent, or Firm*—Reid S. Willis

[57] ABSTRACT

A crude vinylically unsaturated product formed from a palladium-complex-catalyzed reaction of a reactant halide selected from the group consisting of aryl, allyl, vinyl, and benzyl halides, and a reactant olefin having a vinylic hydrogen, wherein the reaction is carried out in the presence of a hydrogen halide acceptor, is purified by first contacting the crude product with a base that is stronger than the hydrogen halide acceptor, then heating the stronger base-contacted product. The purified product shows a marked reduction in concentration bromine and palladium impurities. The product can then be further purified by such methods as chromatography, crystallization, or distillation to achieve a product that is more suitable for applications where very low levels of inorganic impurities are required.

20 Claims, No Drawings

PROCESS FOR PURIFYING VINYLICALLY UNSATURATED COMPOUNDS PREPARED USING A PALLADIUM-COMPLEX CATALYST

BACKGROUND OF THE INVENTION

This invention relates to an improved process of purifying a vinylically unsaturated compound prepared from the palladium-complex catalyzed reaction of an olefin containing a vinylic hydrogen and an aryl, allyl, vinyl, or benzyl halide. Specifically, the invention relates to an improved method of removing palladium and halide from the vinylically unsaturated compound.

The palladium-complex catalyzed vinylation of organic halides is described by Heck in U.S. Pat. No. 3,922,299 and in Organic Reactions, vol. 27, p. 345 (1982), both incorporated herein by reference. The reaction is represented by the following equation:

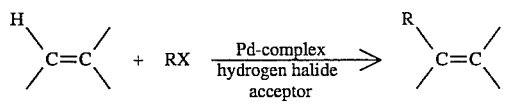

wherein R is aryl, allyl, vinyl, or benzyl, the Pd-complex is typically palladium bound to a trivalent organophosphorous or organoarsenic moiety, and an organic or halo moiety. Heck teaches that the reaction can be carried out with or without a solvent, with suggested solvents being acetonitrile, tetrahydrofuran, methanol, dimethylformamide (DMF), and N-methyl-pyrrolidinone.

In U. S. Pat. No. 5,264,646, incorporated herein by reference, DeVries et al. discloses an improved process for the Heck-type vinylation reaction, wherein the reaction is carried out in a water-containing medium.

The crude vinylically unsaturated compound prepared by the methods described by Heck and DeVries et al. is advantageously purified to remove inorganics, particularly palladium and halide, from the crude product. This purification is particularly crucial, for example, for high performance electronic applications, where it is often necessary to reduce inorganic impurity concentrations to low ppm levels. Present purification processes, such as distillation, crystallization, or chromatography, are necessary, yet often insufficient for reducing these inorganic impurities to the desired levels. Indeed, multiple purification steps may be required to achieve the desired reduction of impurities. Furthermore, these processes do not provide an easy means for recovering and recycling palladium.

Because the recovery and recyclability of palladium is desirable, and multiple purification steps are undesirable, it would be an advantage to provide a simple means of reducing halide and palladium impurities in the crude vinylically unsaturated compound prior to a further purification step.

SUMMARY OF THE INVENTION

The present invention is an improved process of reducing the concentration of palladium and halide in a crude vinylically unsaturated product that has been extracted with water from a product mixture containing the crude vinylically unsaturated product, the product mixture being formed from a palladium-complex-catalyzed reaction of a reactant halide selected from the group consisting of aryl, allyl, vinyl, and benzyl halides, and a reactant olefin having a vinylic hydrogen; wherein the reaction is carried out in the presence of a hydrogen halide acceptor; the improvement comprising the steps of:

a) contacting the crude vinylically unsaturated product with a base that is stronger than the hydrogen halide acceptor and phase-separable from the product;

b) phase-separating the product in step (a) from the stronger base; then c) heating the separated product of step (b) under conditions such that the palladium can be isolated from the product by filtration or centrifugation; and d) removing the palladium from the product in step (c).

In another aspect, the invention is an improved process of reducing the amount of palladium and bromide in a crude 1,3-divinyl-1,1,3,3-tetramethyldisiloxanebisbenzocyclobutene product that has been extracted with water from a product mixture containing the crude product, the product mixture being formed by a palladium-complex-catalyzed reaction of a 4-bromobenzocyclobutene and 1,3-divinyl-1,1,3,3-tetramethyl-disiloxane; wherein the reaction is carried out in an aqueous solution of 30–70 volume percent of dimethylformamide, and in the presence of potassium acetate or triethylamine, or a mixture thereof; the improvement comprising the steps of:

a) contacting the crude product with aqueous sodium hydroxide;

b) water-extracting the sodium hydroxide from the crude product; then c) heating the extracted crude product of step (b) under sufficient conditions to agglomerate the palladium; and d) removing the agglomerated palladium from the crude product in step (c).

The present invention addresses a need in the art by providing effective post-reaction treatments which reduce palladium and halide impurities in a vinylically unsaturated product prepared by Heck-type chemistry.

DETAILED DESCRIPTION OF THE INVENTION

The post-reaction processes of the present invention are suitable for vinylically unsaturated products derived from reactant aryl, allyl, vinyl, benzyl halides, and reactant olefins such as those described in DeVries et al., U.S. Pat. No. 5,243,068, supra. Preferred reactant halides are substituted or unsubstituted aryl halides. Representative examples include halogenated benzenes and naphthalenes, such as $C_1$–$C_6$ alkylbromobenzene, $C_1$–$C_6$ alkylbromonaphthalenes, and bromobenzocyclobutenes (Br-BCBs). Br-BCBs can be prepared by the method described by Liu in U.S. Pat. No. 4,822,930, incorporated herein by reference. The most preferred aryl halide used in the process of the present invention is 4-bromobenzocyclobutene (4-Br-BCB).

Representative reactant olefins include vinyl, allyl, and methallyl hydrocarbons, such as ethylene, propylene, 1-butene, 2-butene, 2-methyl-l-propene, 1,3-butadiene, 1,4-pentadiene, 1,5-hexadiene, 3-methyl-1-butene, styrene, substituted styrenes, divinylbenzenes, vinylnaphthalenes, stilbene, and allyl cyclohexane; vinyl, allyl, and methallyl compounds containing a heteroatom, such as acrylate and methacrylate esters, acrylonitrile, and methacrylonitrile; vinyl or allyl organosilicon compounds, such as tri-$C_1$-$C_6$-alkylvinylsilanes; and siloxanes represented by the formula:

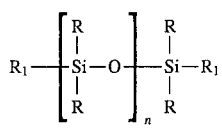

wherein each R is independently $C_1$–$C_6$-alkyl, cycloalkyl, aralkyl, or aryl; $R_1$ is independently vinyl, allyl, or methallyl; and n is an integer from 1 to 4500.

More preferably R1 is vinyl, each R is methyl, ethyl, or phenyl; and n is an integer from 2 to 10. An especially preferred siloxane is 1,3-divinyl-1,1,3,3tetrametyhyldisiloxane.

The most preferred vinylically unsaturated products are prepared from 4-Br-BCB and a mixture of m- and p-vinyltoluene; 4-Br-BCB and divinylbenzene; ethylene and o-bromotoluene; 4-Br-BCB and ethylene; 4-Br-BCB and styrene; and 4-Br-BCB and 1,3-divinyl-1,1,3,3-tetramethyldisiloxane.

The molar ratio of reactant halide to reactant olefin can be determined by routine experimentation. Generally, molar ratios of 0.5:1 to 1.5:1 are preferred for the synthesis of monoadducts, with higher ratios of reactant halide to reactant olefin being preferred for higher adducts.

The reaction is carried out in the presence of a palladium-complex catalyst. The palladium-complex catalyst suitable for the preparation of the vinylically unsaturated product is generally described in U.S. Pat. No. 3,922,299, supra. Preferably, the catalyst is formed from palladium (II) acetate and a triaryl phosphine, such as triphenylphosphine, or tris-(o-tolyl)phosphine.

The reaction requires a hydrogen halide acceptor, which is sufficiently strong to form a salt with a hydrogen halide, especially hydrogen bromide or hydrogen iodide, yet sufficiently weak so as not to deactivate the catalyst or undesirably decompose the reactants or product. Preferred hydrogen halide acceptors include trialkylamines and salts of weak acids and strong bases, such as alkali metal or alkaline earth metal acetates and bicarbonates. More preferred hydrogen halide acceptors for the practice of the present invention are potassium acetate, and triethylamine, with potassium acetate being especially preferred.

The reaction may be carried out with or without a solvent, and is preferably carried out with a solvent. Representative solvents include nitriles, such as acetonitrile; alcohols, such as methanol or ethanol; N,N-dialkylformamides, such as dimethylformamide; N-alkyl pyrrolidinones, such as N-methylpyrrolidinone; glycol ethers, dioxane, tetrahydrofuran, and water.

When the hydrogen halide acceptor is a salt of a weak acid and a strong base, water or a water-containing solvent is advantageously employed; preferably an aqueous solution consisting of about 10 to 0 about 90 volume percent of an organic solvent selected from the group consisting of nitriles, alcohols, N,N-dialkylformamides, N-alkylpyrrolidinones, glycol ethers, dioxane, and tetrahydrofuran; more preferably an aqueous solution of about 30 to about 70 volume percent of dimethylformamide or N-methylpyrrolidinone.

The temperatures suitable for formation of the vinylically unsaturated product vary from about room temperature up to a temperature below which the product or starting materials decompose or polymerize. Reaction temperatures in the range of about 80° C. to about 120° C. are preferred. When the reaction is complete, water is added to the reaction mixture, which comprises the crude vinylically unsaturated product, solvent, and salts, and the aqueous phase is removed. The crude vinylically unsaturated product is ready for post-treatment.

Treatment of Crude Vinylically Unsaturated Product

The term "crude" is used herein to refer to the vinylically unsaturated product prior to purification by chromatography, crystallization, or distillation. The crude vinylically unsaturated product prepared in the manner described by Heck or DeVries et al. is first contacted with a base that is stronger than the hydrogen halide acceptor. The stronger base is water-extractable from the vinylically unsaturated product, and may be added to the product in an aqueous or non-aqueous form. If the hydrogen halide acceptor is an alkali metal or alkaline earth metal acetate, preferred stronger bases include alkali metal or alkaline earth metal hydroxides, such as lithium hydroxide, sodium hydroxide, potassium hydroxide, calcium hydroxide, or magnesium hydroxide; trialkylamines, such as triethylamine, trimethylamine, or tri-n-butylamine; an alkali metal ethylenediamine tetramine (EDTA), such as tetrasodium EDTA; a carbonate, such as potassium carbonate or sodium carbonate; or an alkoxide, such as sodium methoxide and sodium ethoxide. 5 Aqueous sodium hydroxide, preferably about 0.02, more preferably from about 0.05, and most preferably from about 0.1 weight percent, to about 10, more preferably to about 5, and most preferably to about 2 weight percent aqueous sodium hydroxide, is an especially preferred stronger aqueous base for alkali metal or alkaline earth metal acetates or bicarbonates, as well as trialkylamines.

The stronger base is contacted with the product in such a manner and in sufficient quantity to transfer halide from the product to the stronger base. Preferably, the stronger base is added to the crude product with stirring at a temperature in the range from about 25° C., more preferably from 40° C., and most preferably from about 50° C., to preferably about 90° C., more preferably to about 75° C., and most preferably to about 60° C. When an aqueous base is used, the pH of the aqueous phase is preferably in range of about 10, more preferably from about 11, to about 14, more preferably to about 13.

Though not bound by theory, it is believed that the stronger base dehydrohalogenates hydrohalogenated impurities in the product, thereby converting at least a portion of such impurities to useful product; concomitantly, the dehydrohalogenation process serves to reduce the amount of halide in the crude product mixture. The following reaction scheme illustrates this point:

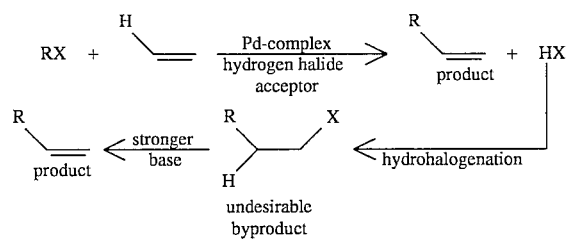

It is also possible that the stronger base may dehalogenate the post-reacted palladium-complex catalyst, thereby reducing the stability of the complex and allowing the palladium metal to be more readily recoverable in a subsequent heat treatment step.

It has been discovered that certain strong bases, such as alkali metal hydroxides and alkoxides, when used as hydrogen halide acceptors, undesirably deactivate the palladium-complex catalyst. Therefore, these catalyst-deactivating strong bases are not useful as hydrogen halide acceptors, even though they would be expected to suppress the formation of hydrohalogenated byproducts. However, the combination of a non-catalyst-deactivating weaker base used in the reaction medium, followed by post-reaction treatment with a stronger base that is capable of removing halide from the product, provides improved purification without significant yield loss.

A solvent which is miscible with the product, but immiscible with water is advantageously added to the crude product to promote the separation of the stronger base from the product. Preferred solvents include hydrocarbon solvents, such as xylene, mesitylene, toluene, and petroleum ethers, such as Isopar G.

The product and optionally a solvent for the product are phase-separated from the stronger base by extracting the stronger base with water. The isolated product, or the product and solvent, is then heated under conditions such that the palladium can be recovered from the product by filtration or centrifugation without decomposing or polymerizing the product. At a sufficiently high temperature, preferably in the range from about 100° C., more preferably from about 120° C., to about 180° C., more preferably to about 150° C., palladium agglomerates out of the aqueous base treated product. This agglomerated palladium is preferably recovered by filtration through a filter having a pore size of less than 2 microns, more preferably less than 0.5 micron, and most preferably less than 0.2 micron.

The combination of aqueous base treatment followed by heat treatment results in a vinylically unsaturated product that contains a significant reduction in halide and palladium impurities. If the palladium-complex catalyst used to prepared the vinylically unsaturated product contains phosphorous, the crude product that has been subjected to treatment with a stronger base, and prior to heat treatment, is advantageously treated with a peroxide, such as aqueous hydrogen peroxide or t-butyl hydroperoxide to oxidize phosphine residues to corresponding phosphine oxides. These phosphine oxides can then be removed, for example, by passing the crude product through a phosphine oxide adsorbing medium, such as a silica gel column. The treated crude product can also be purified further by means such as crystallization, distillation, or chromatography. The post-reaction processes described herein have the advantage of isolating impurities in a single location, thereby making recovery and reuse of palladium easier.

The following example is provided to illustrate the process of present invention but is not intended to limit the scope thereof.

EXAMPLE

Synthesis and Purification of -1,3-divinyl-1,1,3,3-tetramethyldisiloxanebisbenzocyclobutene (DVS-bisBCB)

Potassium acetate (870 g) and deionized water (420 mL) are charged into a 5 L thermowell three-neck flask, equipped with an overhead electric agitator with a teflon stirshaft, a thermocouple-controlled heating mantle with a timer and a high-temperature shutoff, a nitrogen inlet atop a condenser leading to an oil bubbler, and a glass funnel. The reactor is purged with nitrogen, warmed to 40° C. and stirred. When the potassium acetate is dissolved, 4-BrBCB (560 g) and 1,3-divinyl-1,1,3,3-tetramethyldisiloxane (280 g) are added to the reactor with DMF rinsing. Palladium (II) acetate (0.84 g) and tris-(o-tolyl)phosphine (4.56 g) are dissolved with about 100 g of DMF, and the dissolved catalyst mix is added to the reactor with DMF rinses. The total amount of DMF used is 840 mL. The reactor is sparged with nitrogen for 25 minutes using the condenser as the outlet. The reaction temperature is raised to 94° C. The reaction is complete at 24 hours, as determined by GC-analyzed disappearance of Br-BCB.

Deionized water (1.2 L) is added with stirring and the temperature is adjusted to 60° C. The aqueous phase is separated from the organic phase. An aliquot of the organic phase is mixed with Isopar G, and washed 3 times with deionized water. The Isopar G is removed and the aliquot is found to contain 182 ppm bromine and 606 ppm palladium by neutron activation analysis. Aqueous sodium hydroxide (0.5 weight percent NaOH, 1.2 L) is added to the reaction mixture with stirring for 4 hours at 60° C. Isopar G (600 g) is then added to the mixture, the aqueous phase is removed, and the organic layer is extracted with three 1.6-L portions of water, whereupon the pH of the last aqueous layer is reduced to 8. An aliquot of the sodium hydroxide-washed, water-washed organic phase is found to contain 15 ppm Br and 602 ppm palladium after removal of the Isopar G.

t-Butyl hydroperoxide (2.3 g) is added to the organic phase, which is then heated to 60° C. for 6 hours. An aliquot of the hydroperoxide-treated organic phase is filtered through a 0.2 micron filter, and the filtrate is found to contain 15 ppm Br and 608 ppm palladium after removal of the Isopar G.

The product mixture is then heated to 120° C. for 6 hours, whereupon the mixture turns black from agglomerated palladium. The mixture is then cooled to room temperature and passed through a 0.2 micron filter, where the agglomerated palladium is recovered. An aliquot of the filtrate, which is a clear yellow color, is found to contain 10 ppm Br and 9 ppm palladium after removal of Isopar G.

The reaction product is then passed through a column containing 220 g of silica gel and 22 g of $MgSO_4$. The column is rinsed with two 400-g portions of Isopar G. The Isopar G is distilled from the the combined effluents, and the product is distilled through a short-path molecular distillation unit. The chromatographed and distilled product is found to contain 1.5 ppm Br and less than 0.5 ppm palladium as determined by neutron activation analysis.

What is claimed is:

1. In an improved process of reducing the concentration of palladium and halide in a crude vinylically unsaturated product that has been extracted with water from a product mixture containing the crude vinylically unsaturated product, the product mixture being formed from a palladium-complex-catalyzed reaction of a reactant halide selected from the group consisting of aryl, allyl, vinyl, and benzyl halides, and a reactant olefin having a vinylic hydrogen; wherein the reaction is carried out in the presence of a hydrogen halide acceptor; the improvement comprising the steps of:

a) contacting the crude vinylically unsaturated product with a base that is stronger than the hydrogen halide acceptor and phase-separable from the product;

b) phase-separating the product in step (a) from the stronger base; then c) heating the separated product of step (b) under conditions such that the palladium can be isolated from the product by filtration or centrifugation; and d) removing the palladium from the product in step (c).

2. The process of claim 1 wherein the palladium complex is formed from palladium (II) acetate and tris-(o-toly)phosphine.

3. The process of claim 1 wherein the hydrogen halide acceptor comprises an alkali metal acetate.

4. The process of claim 1 wherein the hydrogen halide acceptor is trialkylamine or an alkali metal acetate or a combination thereof.

5. The process of claim 3 wherein the second base comprises an alkali metal hydroxide, an alkali metal EDTA, or a trialkylamine.

6. The process of claim 1 wherein the reaction is carried out in a solvent which is an aqueous solution consisting of up to 90 volume percent of an organic solvent selected from the group consisting of nitriles, alcohols, N,N-dialkylformamides, N-alkylpyrrolidinones, glycol ethers, dioxane, and tetrahydrofuran.

7. The process of claim 6 wherein the solvent is an aqueous solution of 30–70 volume percent of dimethylformamide or N-methylpyrrolidinone.

8. The process of claim 1 wherein the reactant olefin having a vinylic hydrogen is a vinylically unsaturated organosilicon compound having the structure:

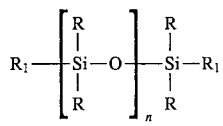

wherein each R is independently $C_1$–$C_6$-alkyl, cycloalkyl, aralkyl, or aryl; $R_1$ is independently vinyl, allyl, or methallyl; and n is an integer from 1 to 4500.

9. The process of claim 8 wherein $R_1$ is vinyl, each R is methyl, ethyl, or phenyl; and n is an integer from 2 to 10.

10. The process of claim 8 wherein the vinylically unsaturated organosilicon compound is 1,3-divinyl-1,1,3,3-tetramethyldisiloxane.

11. The process of claim 1 wherein in step (c) the separated product is heated to between about 100° C. and about 150° C.

12. The process of claim 5 wherein the stronger base is aqueous sodium hydroxide.

13. The process of claim 12 wherein the reactant halide is an aryl bromide.

14. The process of claim 13 reactant halide is 4-bromobenzocyclobutene and the hydrogen halide acceptor is potassium acetate.

15. In an improved process of reducing the amount of palladium and bromide in a crude 1,3-divinyl-1,1,3,3-tetramethyldisiloxane-bisbenzocyclobutene product that has been extracted with water from a product mixture containing the crude product, the product mixture being formed by a palladium-complex-catalyzed reaction of a 4-bromobenzocyclobutene and 1,3-divinyl-1,1,3,3-tetramethyldisiloxane; wherein the reaction is carried out in an aqueous solution of 30–70 volume percent of dimethylformamide, and in the presence of potassium acetate or triethylamine, or a mixture thereof; the improvement comprising the steps of:

a) contacting the crude product with aqueous sodium hydroxide;

b) water-extracting the sodium hydroxide from the crude product; then c) heating the extracted crude product of step (b) under sufficient conditions to agglomerate the palladium; and d) removing the agglomerated palladium from the crude product in step (c).

16. The process of claim 15 wherein the palladium complex is formed from palladium (II) acetate and tris-(o-tolyl)phosphine.

17. The process of claim 16 wherein after step (b), and prior to step (c), the extracted crude product is treated with t-butyl hydroperoxide, and the crude product from step (d) is passed through a silica gel column.

18. The process of claim 17 wherein in step (c) the crude product is heated to between about 100° C. and about 150° C.

19. The process of claim 18 wherein the agglomerated palladium is removed from the crude product by filtration through a filter having a pore size of less than 0.2 microns.

20. The process of claim 15 wherein the crude product from step (d) is further purified by chromatography, distillation, crystallization, or a combination thereof.

* * * * *